United States Patent
Li et al.

(10) Patent No.: US 9,970,267 B2
(45) Date of Patent: May 15, 2018

(54) EXPERIMENTAL DEVICE FOR SIMULATING EXPLOITATION OF NATURAL GAS HYDRATE IN PERMEABLE BOUNDARY LAYER

(71) Applicant: GUANGZHOU INSTITUTE OF ENERGY CONVERSION, CHINESE ACADEMY OF SCIENCES, Guangzhou, Guangdong Province (CN)

(72) Inventors: Xiaosen Li, Guangzhou (CN); Yu Zhang, Guangzhou (CN); Yi Wang, Guangzhou (CN); Gang Li, Guangzhou (CN); Zhaoyang Chen, Guangzhou (CN); Chungang Xu, Guangzhou (CN)

(73) Assignee: GUANGZHOU INSTITUTE OF ENERGY CONVERSION, CHINESE ACADEMY OF SCIENCES, Guangdong (CN)

( * ) Notice: Subject to any disclaimer, the term of this patent is extended or adjusted under 35 U.S.C. 154(b) by 270 days.

(21) Appl. No.: 14/765,475

(22) PCT Filed: Nov. 5, 2014

(86) PCT No.: PCT/CN2014/090331
§ 371 (c)(1),
(2) Date: Aug. 3, 2015

(87) PCT Pub. No.: WO2016/061854
PCT Pub. Date: Apr. 28, 2016

(65) Prior Publication Data
US 2016/0251943 A1 Sep. 1, 2016

(30) Foreign Application Priority Data

Oct. 20, 2014 (CN) .......................... 2014 1 0559230

(51) Int. Cl.
*E21B 41/00* (2006.01)
*B01J 12/02* (2006.01)
(Continued)

(52) U.S. Cl.
CPC .......... *E21B 41/0092* (2013.01); *B01J 12/02* (2013.01); *C10L 3/108* (2013.01); *C10L 2290/60* (2013.01);
(Continued)

(58) Field of Classification Search
CPC ............ E21B 41/00; B01J 12/02; C10L 3/108
(Continued)

(56) References Cited

U.S. PATENT DOCUMENTS 3,477,364 A * 11/1969 Berry ....................... A63D 9/00
100/211
5,162,235 A * 11/1992 Hardy ..................... G01N 5/00
436/139

(Continued)

FOREIGN PATENT DOCUMENTS

CN         101963057 A  *  2/2011

OTHER PUBLICATIONS

Google translation of CN-101963057 A—Mar. 28, 2017.*

*Primary Examiner* — Huy-Tram Nguyen
(74) *Attorney, Agent, or Firm* — Westerman, Hattori, Daniels & Adrian, LLP

(57) ABSTRACT

A device for simulating exploitation of a natural gas hydrate in a permeable boundary layer includes a high pressure reaction kettle, a formation simulation unit and an aquifer maintaining unit. A water bath jacket externally connected with constant temperature water bath is arranged on the outer wall of the high pressure reaction kettle for providing a necessary temperature condition for the high pressure reaction kettle. A simulative well at the center of the top of (Continued)

the high pressure reaction kettle is connected with liquid injection, gas injection, gas production and water production equipment. An aquifer interface at the bottom of the high pressure reaction kettle is connected to the aquifer maintaining unit through a pipeline. The simulation device simulates the geological environment of a hydrate reservoir, allowing comprehensive evaluation of hydrate exploitation under different formation permeability and different formation pressure gradients.

9 Claims, 1 Drawing Sheet

(51) Int. Cl.
    *C10L 3/10*     (2006.01)
    *E21B 43/16*     (2006.01)
    *G01N 15/08*     (2006.01)
    *G01N 33/24*     (2006.01)

(52) U.S. Cl.
    CPC .......... *E21B 43/16* (2013.01); *G01N 15/0826* (2013.01); *G01N 33/24* (2013.01)

(58) Field of Classification Search
    USPC ........................................................ 422/130
    See application file for complete search history.

(56) References Cited

U.S. PATENT DOCUMENTS

| | | | | |
|---|---|---|---|---|
| 5,540,190 | A * | 7/1996 | Rogers | .................... F02B 43/00 123/1 A |
| 2010/0139378 | A1* | 6/2010 | Chuvilin | .................. G01N 5/02 73/73 |
| 2011/0207848 | A1* | 8/2011 | Hirata | .................. B29C 73/163 523/166 |
| 2012/0222870 | A1* | 9/2012 | Schaef | ................ E21B 41/0064 166/402 |

* cited by examiner

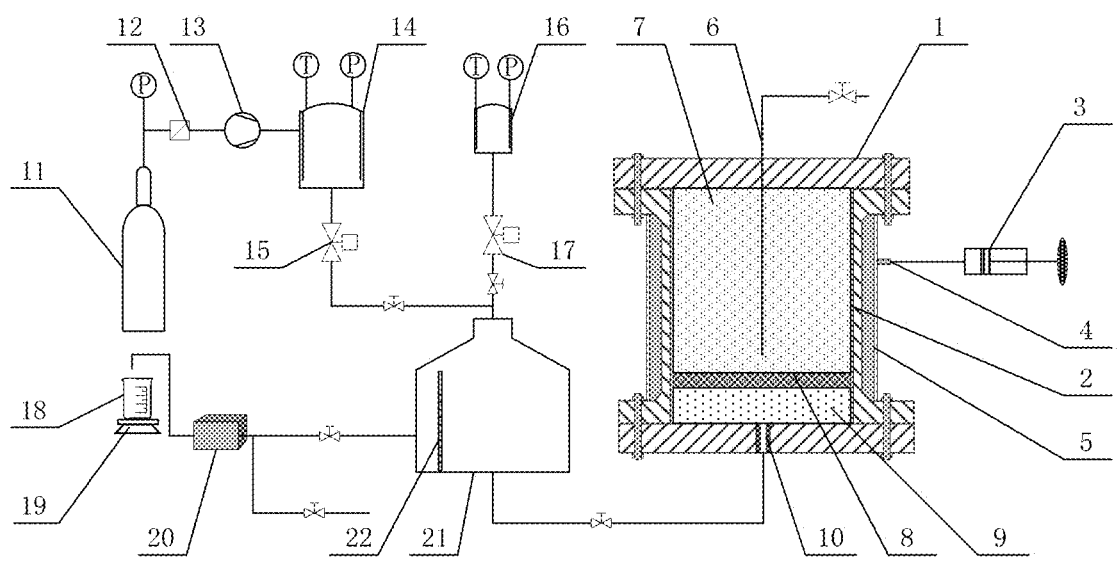

EXPERIMENTAL DEVICE FOR SIMULATING EXPLOITATION OF NATURAL GAS HYDRATE IN PERMEABLE BOUNDARY LAYER

FIELD OF THE INVENTION

The present invention relates to the field of natural gas hydrate development, provides a set of experimental devices for performing relevant simulation researches under actual geological environments, and particularly relates to an experimental device for simulating exploitation of a natural gas hydrate in a permeable boundary layer.

BACKGROUND OF THE INVENTION

A natural gas hydrate refers to a cage-like crystal matter generated by a natural gas and water at a certain temperature and pressure and can exist in the nature in a variety of ways. Due to the huge reserves and the clean and efficient properties, the natural gas hydrate is considered as a potential alternative energy. If the natural gas hydrate can be effectively, quickly and economically exploited, the increasing energy pressure can be alleviated. Therefore, research on a natural gas hydrate exploitation method is an important issue to be urgently solved in the field of oil and gas engineering.

The existing exploitation methods can be generally divided into three categories: a thermal exploitation method, a chemical agent exploitation method and a pressure reducing exploitation method. The pressure reducing exploitation method is proposed earliest and is considered to be a simple, economical and effective method, which is mainly used for reducing the pressure of a hydrate reservoir to be lower than the balance decomposition pressure of the natural gas hydrate so as to promote the natural gas hydrate to decompose, and the exploitation of a free gas below a hydrate layer is an effective method for reducing the reservoir pressure. However, the pressure reducing method also has the defects of slow hydrate decomposition rate and long exploitation period. Meanwhile, since the natural gas hydrate mainly exists in deepwater seabed sediments, how to reduce the pressure is a difficult problem. A numerical simulation research finds that due to the permeation of seawater on the hydrate reservoir in a pressure reducing process, a huge water yield severely influences the pressure reducing efficiency and the hydrate decomposition rate. At present, the research on the natural gas hydrate exploitation technology is mainly achieved by laboratory simulation, but the existing experiment equipment is relatively simple, a constant volume method is mainly adopted to synthesize and decompose the hydrate, which is hard to truly simulate actual marine geological conditions, in particular, due to the lack of experiment equipment used for simulating a penetration process of seawater and an aquifer on the natural gas hydrate reservoir, an experimental simulation result is not matched with a numerical simulation result and the hydrate exploitation process under actual geological conditions is difficult to truly reflect.

SUMMARY OF THE INVENTION

Aiming at the above-mentioned deficiencies, the present invention provides a device for simulating exploitation of a natural gas hydrate in a permeable boundary layer, wherein a high pressure reaction kettle, a formation simulation unit and an aquifer maintaining unit are used for truly simulating the geological environment of a hydrate reservoir, so as to comprehensively evaluate the accumulation and exploitation processes more truly and provide guidance for natural gas hydrate exploitation.

To fulfill the above-mentioned object, the present invention adopts the following solution:

a device for simulating exploitation of a natural gas hydrate in a permeable boundary layer, including a high pressure reaction kettle, a formation simulation unit and an aquifer maintaining unit, wherein a water bath jacket externally connected with constant temperature water bath is arranged on the outer wall of the high pressure reaction kettle for providing a necessary temperature condition for the high pressure reaction kettle, a simulative well externally connected with liquid injection, gas injection, gas production and water production equipment is arranged at the center of the top of the high pressure reaction kettle, an aquifer interface is arranged at the bottom of the high pressure reaction kettle, the formation simulation unit is arranged in the high pressure reaction kettle, and the aquifer maintaining unit is connected with the aquifer interface through a pipeline.

The interior of the high pressure reaction kettle is cylindrical, a confining pressure jacket is arranged in the high pressure reaction kettle, and the confining pressure jacket is connected with a confining pressure pump through a confining pressure interface so as to control a confining pressure through the confining pressure pump.

The formation simulation unit includes a hydrate layer, a low permeability layer and an aquifer, the hydrate layer, the low permeability layer and the aquifer are arranged in the confining pressure jacket from top to bottom, and the confining pressure is loaded to avoid gas and water streaming between different simulative formations.

Quartz sand is filled in the hydrate layer, and a necessary solution and a necessary gas are injected from the simulative well to form the hydrate.

The low permeability layer is a ceramic plate, and the permeability and the thickness of the ceramic plate are prepared according to experimental requirements.

The aquifer is porous conglomerate.

The aquifer maintaining unit includes a nitrogen cylinder, a pressure reducing valve, a gas booster pump, a high pressure gas storage tank, a first pressure control valve, a low pressure gas storage tank, a second pressure control valve, a liquid storage container, an electronic balance, a constant-flux pump and a liquid storage tank, wherein:

the bottom of the liquid storage tank is connected with the aquifer interface through a pipeline so as to be connected with the aquifer for supplementing water in the aquifer and maintaining the pressure of the aquifer;

the nitrogen cylinder is connected with the high pressure gas storage tank through the pressure reducing valve and the gas booster pump in sequence; the high pressure gas storage tank is connected with the liquid storage tank through the first pressure control valve, and high pressure nitrogen is injected from the high pressure gas storage tank into the liquid storage tank through the first pressure control valve to maintain the pressure of the aquifer and simulate the pressure difference of the aquifer and the hydrate layer;

the liquid storage container is placed on the electronic balance, and the liquid storage container is connected with the liquid storage tank through the constant-flux pump for supplementing water to the liquid storage tank;

the top of the liquid storage tank is connected with the low pressure gas storage tank through the second pressure control valve.

A liquid level meter is arranged in the liquid storage tank for measuring the residual water amount in the liquid storage tank.

When the residual water amount in the liquid storage tank is smaller than ⅓, water in the liquid storage container is injected into the liquid storage tank through the constant-flux pump for supplementing water to the liquid storage tank.

In a process of supplementing water to the liquid storage tank, the first pressure control valve is closed, meanwhile the second pressure control valve is opened to inject the gas exhausted by the water into the low pressure gas storage tank to maintain the stable pressure of the liquid storage tank and the aquifer, and the seepage quantity from the aquifer to the hydrate layer is calculated according to the pressure changes and the water injection amounts in the high pressure gas storage tank and the low pressure gas storage tank.

To sum up, the present invention has the advantages that the experimental device in the present invention can truly simulate the geological environment of the hydrate reservoir, so as to comprehensively evaluate the accumulation and exploitation processes more truly and provide guidance for natural gas hydrate exploitation. The experiment process of the simulation system is simple and feasible, and the simulation processes have strong operability and practical values.

BRIEF DESCRIPTION OF THE DRAWINGS

FIG. 1 is a schematic diagram of a structure of an embodiment of the present invention.

REFERENCE NUMERALS 1. high pressure reaction kettle, 2. confining pressure jacket, 3. confining pressure pump, 4. confining pressure interface, 5. water bath jacket, 6. simulative well, 7. hydrate layer, 8. low permeability layer, 9. aquifer, 10. aquifer interface, 11. nitrogen cylinder, 12. pressure reducing valve, 13. gas booster pump, 14. high pressure gas storage tank, 15. pressure control valve, 16. low pressure gas storage tank, 17. pressure control valve, 18. liquid storage container, 19. electronic balance, 20. constant-flux pump, 21. liquid storage tank, 22. liquid level meter.

DETAILED DESCRIPTION OF THE EMBODIMENTS

To better understand the present invention, a further description of the present invention will be given below in combination with the accompanying drawings, but the embodiment of the present invention is not limited thereto.

Embodiment

The structure diagram of a system for simulating exploitation of a natural gas hydrate in a permeable boundary layer in the present invention is as shown in FIG. 1. The system includes a high pressure reaction kettle 1, a formation simulation unit and an aquifer maintaining unit. The interior of the high pressure reaction kettle 1 is cylindrical, a confining pressure jacket 2 is arranged in the high pressure reaction kettle, a water bath jacket 5 is arranged on the outer wall of the high pressure reaction kettle 1 and can be externally connected with constant temperature water bath for providing a necessary temperature condition; a simulative well 6 is arranged at the center of the top of the high pressure reaction kettle 1, and the simulative well 6 can be externally connected with liquid injection, gas injection, gas production and water production equipment. The formation simulation unit includes a hydrate layer 7, a low permeability layer 8 and an aquifer 9. The aquifer maintaining unit includes a nitrogen cylinder 11, a pressure reducing valve 12, a gas booster pump 13, a high pressure gas storage tank 14, a pressure control valve 15, a low pressure gas storage tank 16, a pressure control valve 17, a liquid storage container 18, an electronic balance 19, a constant-flux pump 20, a liquid storage tank 21 and a liquid level meter 22.

Quartz sand is filled in the hydrate layer 7, and a necessary solution and a necessary gas are injected from the simulative well 6 in the high pressure reaction kettle 1 to form the hydrate. The low permeability layer 8 is a ceramic plate with low permeability, and the permeability and the thickness of the ceramic plate are prepared according to experimental requirements. The aquifer 9 is porous conglomerate with high permeability.

A confining pressure jacket 2 is connected with a confining pressure pump 3 through a confining pressure interface 4, and a confining pressure is controlled by the confining pressure pump 3. The hydrate layer 7, the low permeability layer 8 and the aquifer 9 are arranged in the confining pressure jacket 2 from top to bottom, and the confining pressure is loaded to avoid gas and water streaming between different simulative formations.

The bottom of the liquid storage tank 21 in the aquifer maintaining unit is connected with the aquifer interface 10 at the bottom of the high pressure reaction kettle 1 through a pipeline and is connected with the aquifer 9 for supplementing water in the aquifer 9 and maintaining the pressure of the aquifer 9.

The nitrogen cylinder 11 in the aquifer maintaining unit is connected with the high pressure gas storage tank 14 through the pressure reducing valve 12 and the gas booster pump 13; the high pressure gas storage tank 14 is connected with the liquid storage tank 21 through the pressure control valve 15. High pressure nitrogen is injected from the high pressure gas storage tank 14 into the liquid storage tank 21 through the pressure control valve 15 to maintain the pressure of the aquifer 9 and simulate the pressure difference of the aquifer 9 and the hydrate layer 7.

The liquid storage container 18 is connected with the liquid storage tank 21 through the constant-flux pump 20 for supplementing water in the liquid storage tank 21. The liquid level meter 22 is arranged in the liquid storage tank 21 for observing the residual water amount in the liquid storage tank 21. The top of the liquid storage tank 21 is connected with the low pressure gas storage tank 16 through the pressure control valve 17. When the residual water amount in the liquid storage tank 21 is smaller than ⅓, water in the liquid storage container 18 is injected into the liquid storage tank 21 through the constant-flux pump 20. In a process of supplementing water, the pressure control valve 15 is closed, meanwhile the pressure control valve 17 is opened to inject the gas exhausted from the liquid storage tank 21 by the water entering the liquid storage tank 21 in the process of supplementing water into the low pressure gas storage tank 16, so as to maintain the stable pressure of the liquid storage tank 21 and the aquifer 9. The seepage quantity from the aquifer 9 to the hydrate layer 7 is calculated according to the pressure change and the water injection amount measured by the liquid level meter 22. The calculation equation of the seepage quantity is shown by the following formula:

$$Q = W_1 - W_2 + W_i \qquad (1)$$

in the formula:

Q: seepage quantity from the aquifer 9 to the hydrate layer 7.

W1: initial water amount of the liquid storage tank.

W2: real-time water amount of the liquid storage tank.

Wi: water injection amount of the liquid storage tank in the experiment process.

It should be understood that, the application of the present invention is not limited to the examples mentioned above, those of ordinary skill in the art can make improvements or variations according to the above-mentioned illustration, and all these improvements and variations shall fall within the protection scope of the appended claims of the present invention.

The invention claimed is:

1. A device for simulating exploitation of a natural gas hydrate in a permeable boundary layer, comprising:
    a high pressure reaction kettle;
    a formation simulation unit;
    an aquifer maintaining unit;
    a water bath jacket externally connected with a constant temperature water bath and arranged on the outer wall of the high pressure reaction kettle for providing a necessary temperature condition for the high pressure reaction kettle;
    a simulative well externally connected with a liquid injection, a gas injection, a gas production and a water production equipment and arranged at a center of a top of the high pressure reaction kettle; and
    an aquifer interface arranged at the bottom of the high pressure reaction kettle, the formation simulation unit being arranged in the high pressure reaction kettle, and the aquifer maintaining unit is connected with the aquifer interface through a pipeline,
    wherein the aquifer maintaining unit comprises:
        a nitrogen cylinder;
        a pressure reducing valve;
        a gas booster pump;
        a high pressure gas storage tank;
        a first pressure control valve;
        a low pressure gas storage tank;
        a second pressure control valve;
        a liquid storage container;
        an electronic balance;
        a constant-flux pump; and
        a liquid storage tank,
    wherein the bottom of the liquid storage tank is connected with the aquifer interface through a pipeline so as to be connected with the aquifer for supplementing water in the aquifer and maintaining the pressure of the aquifer,
    wherein the nitrogen cylinder is connected with the high pressure gas storage tank through the pressure reducing valve and the gas booster pump in sequence,
    wherein the high pressure gas storage tank is connected with the liquid storage tank through the first pressure control valve, and high pressure nitrogen is injected from the high pressure gas storage tank into the liquid storage tank through the first pressure control valve to maintain the pressure of the aquifer and simulate the pressure difference of the aquifer and the hydrate layer,
    wherein the liquid storage container is placed on the electronic balance, and the liquid storage container is connected with the liquid storage tank through the constant-flux pump for supplementing water to the liquid storage tank, and
    wherein the top of the liquid storage tank is connected with the low pressure gas storage tank through the second pressure control valve.

2. The device for simulating exploitation of the natural gas hydrate in the permeable boundary layer of claim 1,
    wherein an interior of the high pressure reaction kettle is cylindrical, and
    further comprising a confining pressure jacket arranged in the high pressure reaction kettle, the confining pressure jacket being connected with a confining pressure pump through a confining pressure interface to control a confining pressure through the confining pressure pump.

3. The device for simulating exploitation of the natural gas hydrate in the permeable boundary layer of claim 2, wherein the formation simulation unit comprises:
    a hydrate layer;
    a low permeability layer; and
    an aquifer,
    the hydrate layer, the low permeability layer and the aquifer being arranged in the confining pressure jacket from top to bottom, and the confining pressure is loaded to avoid gas and water streaming between different simulative formations.

4. The device for simulating exploitation of the natural gas hydrate in the permeable boundary layer of claim 3, wherein quartz sand is filled in the hydrate layer, and a necessary solution and a necessary gas are injected through the simulative well to form the hydrate.

5. The device for simulating exploitation of the natural gas hydrate in the permeable boundary layer of claim 3, wherein the low permeability layer is a ceramic plate, and a permeability and a thickness of the ceramic plate are prepared according to experimental requirements.

6. The device for simulating exploitation of the natural gas hydrate in the permeable boundary layer of claim 3, wherein the aquifer is a porous conglomerate.

7. The device for simulating exploitation of the natural gas hydrate in the permeable boundary layer of claim 3, wherein a liquid level meter is arranged in the liquid storage tank for measuring the residual water amount in the liquid storage tank.

8. The device for simulating exploitation of the natural gas hydrate in the permeable boundary layer of claim 7, wherein when the residual water amount in the liquid storage tank is smaller than ⅓, water in the liquid storage container is injected into the liquid storage tank through the constant-flux pump for supplementing water to the liquid storage tank.

9. The device for simulating exploitation of the natural gas hydrate in the permeable boundary layer of claim 8, wherein when supplementing water to the liquid storage tank, the first pressure control valve is closed, meanwhile the second pressure control valve is opened to inject the gas exhausted by the water into the low pressure gas storage tank to maintain the stable pressure of the liquid storage tank and the aquifer,
    wherein a seepage quantity from the aquifer to the hydrate layer is calculated according to a pressure change and a water injection amount measured by the liquid level meter, using the following formula:

$$Q = W_1 - W_2 + W_i$$

where:

Q: seepage quantity from the aquifer to the hydrate layer;

W1: initial water amount of the liquid storage tank;

W2: real-time water amount of the liquid storage tank; and

Wi: water injection amount of the liquid storage tank in the experiment process.

* * * * *